(12) United States Patent
Babcock et al.

(10) Patent No.: US 8,232,301 B2
(45) Date of Patent: Jul. 31, 2012

(54) PESTICIDAL COMPOSITIONS

(75) Inventors: Jonathan M. Babcock, Carmel, IN (US); Steven Paul Nolting, Jamestown, IN (US)

(73) Assignee: Dow AgroScience, LLC., Indianapolis, IN (US)

( * ) Notice: Subject to any disclaimer, the term of this patent is extended or adjusted under 35 U.S.C. 154(b) by 349 days.

(21) Appl. No.: 12/537,276

(22) Filed: Aug. 7, 2009

(65) Prior Publication Data

US 2010/0041718 A1 Feb. 18, 2010

Related U.S. Application Data

(60) Provisional application No. 61/088,020, filed on Aug. 12, 2008.

(51) Int. Cl.
*A01N 43/40* (2006.01)
*A01N 59/02* (2006.01)
*A01N 25/30* (2006.01)
*A01P 7/04* (2006.01)

(52) U.S. Cl. ......... 514/357; 514/769; 514/946; 424/710
(58) Field of Classification Search .............. 514/357, 514/769, 946; 424/710
See application file for complete search history.

(56) References Cited

U.S. PATENT DOCUMENTS

2009/0105235 A1* 4/2009 Jeschke et al. ............. 514/229.2

FOREIGN PATENT DOCUMENTS

| EP | 2223598 | * | 9/2010 |
| WO | WO 2007/068355 | | 6/2007 |

OTHER PUBLICATIONS

PCT/US2009/053065, WO, Dow Agrosciences LLC, International Search Report.
PCT/US2009/053065, WO, Dow Agrosciences LLC, Written Opinion.

* cited by examiner

*Primary Examiner* — John Pak
(74) *Attorney, Agent, or Firm* — Carl D. Corvin

(57) ABSTRACT

A pesticidal composition comprising a pesticide, an ammonium salt, and a nonionic surfactant, is provided.

4 Claims, No Drawings

PESTICIDAL COMPOSITIONS

This application claims the benefit of U.S. Provisional Application Ser. No. 61/088,020 filed on Aug. 12, 2008. The invention disclosed in this document is related to the field of pesticides and their use in controlling pests.

FIELD OF THE INVENTION

Background of the Invention

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

DETAILED DESCRIPTION OF THE INVENTION

This invention concerns compositions useful for the control of pests, especially insects, and more especially useful for the control of aphids and other sucking insects.

One component of the pesticidal composition of this invention is a compound of the formula (I)

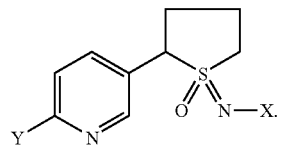

wherein
X represents $NO_2$, CN or $COOR^4$;
L represents a single bond or $R^1$, S and L taken together represents a 4-, 5- or 6-membered ring;
$R^1$ represents $(C_1\text{-}C_4)$ alkyl;
$R^2$ and $R^3$ independently represent hydrogen, methyl, ethyl, fluoro, chloro or bromo;
n is an integer from 0-3;
Y represents $(C_1\text{-}C_4)$ haloalkyl; and
$R^4$ represents $(C_1\text{-}C_3)$ alkyl.
Preferred compounds of formula (I) include the following classes:

(1) Compounds of formula (I) wherein X is $NO_2$ or CN, most preferably CN.
(2) Compounds of formula (I) wherein Y is $CF_3$.
(3) Compounds of formula (I) wherein $R^2$ and $R^3$ independently represent hydrogen, methyl or ethyl.
(4) Compounds of formula (I) wherein $R^1$, S and L taken together form a saturated 5-membered ring, and n is 0, i.e., having the structure

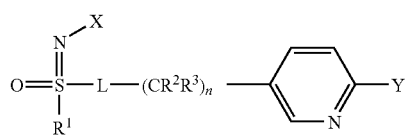

(5) Compounds of formula (I) wherein $R^1$ represents $CH_3$ and L represents a single bond, i.e., having the structure

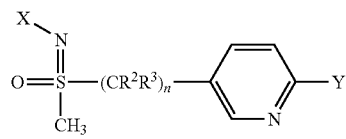

wherein n=1-3, most preferably n=1.

It will be appreciated by those skilled in the art that the most preferred compounds are generally those which are comprised of combinations of the above preferred classes. Furthermore, one or more of these compounds can be used in the pesticidal composition of this invention.

Processes for making these compounds and processes for using these compounds are known in the art. For example, see WO 2007/095229 A2 the entire disclosure of which is hereby incorporated by reference.

Another component of the pesticidal composition of this invention is an ammonium salt (for example, ammonium sulfate, ammonium nitrate, ammonium carbonate, and ammonium phosphates). One or more ammonium salts may be used. Preferably, the ammonium salt is ammonium sulfate. The ammonium salt can be used in its associated form or its disassociated form (which can occur when an ammonium salt is at least partially solubilized). Ammonium salts are available from a wide variety of suppliers.

Another component of the pesticidal composition is a nonionic surfactant. For example, alkyl phenol ethoxylates, fatty alcohol ethoxylates, polyoxyethylene ester of fatty acids, methyl ester ethoxylates, polyalkylene oxide block copolymers, amine oxides, esters of polyhydric alcohols and fatty acids, glycol esters, anhydrohexitol esters, and alkyl poly glycosides. One or more nonionic surfactant may be used. Preferably, polyethoxylated alcohols are used. Nonionic surfactants are available form a wide variety of suppliers.

The weight ratio of amount to use varies considerably depending on the particular components used. However, the following table may be used.

TABLE WR

Concentration ranges of the three components in ppm in a mixture

| Component | Broad | Broader | Broadest |
|---|---|---|---|
| Pesticide | ~0.1 to ~500 | ~0.05 to ~1000 | ~0.01 to ~10,000 |
| Ammonium Salt | ~10,000 to ~22,000 | ~2500 to ~22,000 | ~1000 to ~44,000 |
| Nonionic Surfactant | ~500 to ~2500 | ~250 to ~5000 | ~100 to ~10,000 |

"~" = about

EXAMPLES

The examples are for illustration purposes and are not to be construed as limiting the invention disclosed in this document to only the embodiments disclosed in these examples.

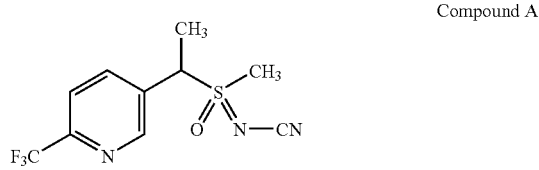

Compound A

Compound A is an insecticide with good activity against sap feeding insects. The molecule has utility as a foliar, soil, and seed treatment. This compound was made in accordance with the methods disclosed in WO 2007/095229 A2.

Materials and Methods. Solutions of nonionic surfactant (Atlox 4991 0.125% and 0.25% V/V; 1250 and 2500 ppm respectively) and ammonium sulfate ("AMS" 10,200 and 20,400 ppm) were prepared in 500 mL of water. Water used to prepare all solutions was obtained from a Milli Q water purification system. Combination mixtures were created by adding surfactant to aliquots of AMS and water solution to create all two-way combinations of surfactant and AMS. A 500 ppm stock solution of Compound A in water was prepared by adding 2 mg of Compound A to 40 mL of water. 62.4 µL of this 500 ppm solution was added to 20 mL of each AMS, surfactant, or surfactant and AMS solution to create 1.56 ppm Compound A high rate solutions. These high rate solutions of Compound A and surfactant, Compound A and AMS, or Compound A, AMS, and surfactant, were serially diluted in two-fold increments with the appropriate surfactant, AMS, or AMS and surfactant combination solutions, to create a dilution series from 1.56 to 0.19 ppm. A dilution series of Compound A in water with no surfactant or AMS was also prepared. All solutions of surfactant, AMS, or surfactant and AMS, were tested without Compound A. Two-to-three-leaf stage cabbage plants were infested on day 1 with green peach aphid, *Myzus persicae* (GPA), by transferring aphid infested foliage to each plant. A uniform number of aphids were transferred based on visual inspection of the infested foliage. Plants were sprayed on all surfaces to wet using a hand held aspirator type sprayer on day 2. Four replicates of each treatment combination were sprayed and all stages of live aphids on each plant were counted on day 4. Data were converted to percent control based on the number of aphids in the unsprayed check treatment. Counts of aphids on unsprayed check plants were used to calculate control for surfactant and AMS solutions. Additionally, the average aphid count on the unsprayed check treatment was used to calculate percent control values for plants sprayed with only Compound A. Aphid counts from plants treated with combinations of Compound A and AMS, surfactant, or AMS and surfactant, were converted to percent control by using the average aphid count from the unsprayed check treatment. Negative percent control values were changed to zero percent control values before assessing treatment combinations for synergy. In general, the efficacy expressed by Compound A at concentrations of 1.56, 0.78 and 0.39 when not combined with surfactant or AMS was great enough that identifying synergy was not practical. So analyses of combinations for synergy were only conducted on the 0.19 ppm rate of Compound A. Homogeneity of variance was tested for measured percent control (actual) and Colby predicted values and these data were found to have homogeneous variances (Levene's test 0.435 P=0.867). Measured efficacy (percent Control) data were compared to calculated Colby values (Colby, S. R. 1967. Calculating Synergistic and Antagonistic Responses of Herbicide Combinations. Weeds 15:20-22) using a two-sided T-test (Minitab). Significant differences (p=0.05) between measured and Colby prediction values indicated that synergy (or antagonism) was present. The formula used to calculate the Colby value for mixtures of Compound A and either surfactant or AMS was:

100−[(100−% control of Compound A rate)*(100−% control of surfactant or AMS)]/100

The formula was adapted for three-way mixtures of Compound A, Surfactant and AMS as follows:

100−[(100−% control of Compound A rate)*(100−% control of surfactant)*(100−% control of AMS)]/10000

An outline of the treatment combinations, percent control and the raw aphid counts obtained for each treatment are presented in Table 1.

TABLE 1

Treatment outline for AMS, nonionic surfactant (NS), and Compound A combinations applied to green peach aphid on cabbage.

| # | A rate (ppm) | NS rate (ppm) | AMS rate (ppm) | Aphid count/plant | | | | % Control (negative values to 0) | | | | Calculated Colby Value | | | |
|---|---|---|---|---|---|---|---|---|---|---|---|---|---|---|---|
| | | | | Rep 1 | Rep 2 | Rep 3 | Rep 4 | Rep 1 | Rep 2 | Rep 3 | Rep 4 | Rep 1 | Rep 2 | Rep 3 | Rep 4 |
| 1 | 0.19 | | | 13 | 7 | 34 | 40 | 53.6 | 63.2 | 29.2 | 25.9 | | | | |
| 2 | | 2500 | | 24 | 31 | 48 | 18 | 14.3 | 0.0 | 0.0 | 66.7 | | | | |
| 3 | | 1250 | | 43 | 50 | 27 | 32 | 0.0 | 0.0 | 43.8 | 40.7 | | | | |
| 4 | | | 20,400 | 35 | 36 | 38 | 31 | 0.0 | 0.0 | 20.8 | 42.6 | | | | |
| 5 | | | 10,200 | 76 | 28 | 104 | 67 | 0.0 | 0.0 | 0.0 | 0.0 | | | | |
| 6 | | 2500 | 20,400 | 43 | 47 | 33 | 25 | 0.0 | 0.0 | 31.3 | 53.7 | | | | |
| 7 | | 2500 | 10,200 | 21 | 3 | 33 | 26 | 25.0 | 84.2 | 31.3 | 51.9 | | | | |
| 8 | | 1250 | 20,400 | 76 | 31 | 9 | 30 | 0.0 | 0.0 | 81.3 | 44.4 | | | | |
| 9 | | 1250 | 10,200 | 67 | 32 | 13 | 15 | 0.0 | 0.0 | 72.9 | 72.2 | | | | |
| 10 | 0.19 | 1250 | | 10 | 8 | 7 | 1 | 64.3 | 57.9 | 85.4 | 98.1 | 53.6 | 63.2 | 60.2 | 56.1 |
| 11 | 0.19 | 2500 | | 23 | 9 | 4 | 4 | 17.9 | 52.6 | 91.7 | 92.6 | 60.2 | 63.2 | 29.2 | 75.3 |
| 12 | 0.19 | | 20,400 | 19 | 24 | 20 | 20 | 32.1 | 0.0 | 58.3 | 63.0 | 56.5 | 64.4 | 43.9 | 57.5 |
| 13 | 0.19 | | 10,200 | 23 | 30 | 28 | 17 | 17.9 | 0.0 | 41.7 | 68.5 | 53.6 | 63.2 | 29.2 | 25.9 |
| 14 | 0.19 | 1250 | 20,400 | 0 | 6 | 1 | 1 | 100.0 | 68.4 | 97.9 | 98.1 | 53.6 | 63.2 | 48.7 | 74.8 |
| 15 | 0.19 | 2500 | 20,400 | 0 | 2 | 2 | 0 | 100.0 | 89.5 | 95.8 | 100.0 | 60.2 | 63.2 | 43.9 | 85.8 |

TABLE 1-continued

Treatment outline for AMS, nonionic surfactant (NS), and Compound A combinations applied to green peach aphid on cabbage.

| # | A rate (ppm) | NS rate (ppm) | AMS rate (ppm) | Aphid count/plant | | | | % Control (negative values to 0) | | | | Calculated Colby Value | | | |
|---|---|---|---|---|---|---|---|---|---|---|---|---|---|---|---|
| | | | | Rep 1 | Rep 2 | Rep 3 | Rep 4 | Rep 1 | Rep 2 | Rep 3 | Rep 4 | Rep 1 | Rep 2 | Rep 3 | Rep 4 |
| 16 | 0.19 | 1250 | 10,200 | 0 | 4 | 1 | 2 | 100.0 | 78.9 | 97.9 | 96.3 | 53.6 | 63.2 | 60.2 | 56.1 |
| 17 | 0.19 | 2500 | 10,200 | 4 | 7 | 13 | 1 | 85.7 | 63.2 | 72.9 | 98.1 | 60.2 | 63.2 | 29.2 | 75.3 |
| 18 | | | | 28 | 19 | 48 | 54 | | | | | | | | |

Results. A summary of measured and Colby predicted values and associated T-test statistical values are included in Table 2. When surfactant or AMS was combined with Compound A there were no instances where synergy could be supported at the 0.05% level. When AMS and surfactant were combined with Compound A three of the combination mixtures (out of 4 possible) produced synergy that was statistically supported (Table 2). This summary indicates significant synergy when Compound A, AMS and surfactant are combined. The statistically increased activity measured for three way combinations in Table 2 reflect increases in activity of 51.6-60.1% compared to Compound A alone.

TABLE 2

Efficacy of 0.19 ppm rates of Compound A when combined with surfactant, AMS or surfactant and AMS.

| A rate (ppm) | NS rate (ppm) | AMS rate (ppm) | % Control | Mean | StDev | SE Mean | T-Test Results |
|---|---|---|---|---|---|---|---|
| 0.19 | 1250 | | Measured | 76.4 | 18.6 | 9.3 | T = 1.90 P = 0.15 |
| | | | Colby Calculated | 58.28 | 4.26 | 2.1 | |
| 0.19 | 2500 | | Measured | 63.7 | 35.8 | 18 | T = 0.33 P = 0.76 |
| | | | Colby Calculated | 57 | 19.6 | 9.8 | |
| 0.19 | | 20,400 | Measured | 38.3 | 29 | 14 | T = −1.14 P = 0.34 |
| | | | Colby Calculated | 55.58 | 8.54 | 4.3 | |
| 0.19 | | 10,200 | Measured | 32 | 29.7 | 15 | T = −0.63 P = 0.56 |
| | | | Colby Calculated | 43 | 18.3 | 9.1 | |
| 0.19 | 1250 | 20,400 | Measured | 91.1 | 15.2 | 7.6 | T = 3.26 P = 0.022*** |
| | | | Colby Calculated | 60.1 | 11.5 | 5.8 | |
| 0.19 | 2500 | 20,400 | Measured | 96.33 | 4.96 | 2.5 | T = 3.68 P = 0.035*** |
| | | | Colby Calculated | 63.3 | 17.2 | 8.6 | |
| 0.19 | 1250 | 10,200 | Measured | 93.28 | 9.7 | 4.9 | T = 6.60 P = 0.0027*** |
| | | | Colby Calculated | 58.28 | 4.26 | 2.1 | |
| 0.19 | 2500 | 10,200 | Measured | 80 | 15.2 | 7.6 | T = 1.85 P = 0.12 |
| | | | Colby Calculated | 57 | 19.6 | 9.8 | |

***Indicates significant synergy of mixture compared to Compound A by itself

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide, potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles).

In another embodiment, the invention disclosed in this document can be used to control Dermaptera (earwigs).

In another embodiment, the invention disclosed in this document can be used to control Dictyoptera (cockroaches).

In another embodiment, the invention disclosed in this document can be used to control Diptera (true flies).

In another embodiment, the invention disclosed in this document can be used to control Hemiptera (true bugs).

In another embodiment, the invention disclosed in this document can be used to control Homoptera (aphids, scales, whiteflies, leafhoppers).

In another embodiment, the invention disclosed in this document can be used to control Hymenoptera (ants, wasps, and bees).

In another embodiment, the invention disclosed in this document can be used to control Isoptera (termites).

In another embodiment, the invention disclosed in this document can be used to control Lepidoptera (moths and butterflies).

In another embodiment, the invention disclosed in this document can be used to control Mallophaga (chewing lice).

In another embodiment, the invention disclosed in this document can be used to control Orthoptera (grasshoppers, locusts, and crickets).

In another embodiment, the invention disclosed in this document can be used to control Phthiraptera (sucking lice).

In another embodiment, the invention disclosed in this document can be used to control Siphonaptera (fleas).

In another embodiment, the invention disclosed in this document can be used to control Thysanoptera (thrips).

In another embodiment, the invention disclosed in this document can be used to control Thysanura (bristletails).

In another embodiment, the invention disclosed in this document can be used to control Acarina (mites and ticks).

In another embodiment, the invention disclosed in this document can be used to control Nematoda (nematodes).

In another embodiment, the invention disclosed in this document can be used to control Symphyla (symphylans).

For more detailed information consult "Handbook of Pest Control—The Behavior, Life History, and Control of Household Pests" by Arnold Mallis, 9th Edition, copyright 2004 by GIE Media Inc.

Mixtures

Some of the pesticides that can be employed beneficially in combination with the invention disclosed in this document include, but are not limited to the following, 1,2-dichloropropane, 1,3-dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, amidithion, amidoflumet, aminocarb, amiton, amitraz, anabasine, arsenous oxide, athidathion, azadirachtin, azamethiphos, azinphos-ethyl, azinphos-methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta-cyfluthrin, beta-cypermethrin, bifenazate, bifenthrin, binapacryl, bioallethrin, bioethanomethrin, biopermethrin, bistrifluron, borax, boric acid, bromfenvinfos, bromo-DDT, bromocyclen, bromophos, bromophos-ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos-methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A&B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap-4, dinocap-6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoatemethyl, ethoprophos, ethyl-DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion-ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, furathiocarb, furethrin, furfural, gamma-cyhalothrin, gamma-HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methylchloroform, methylene chloride, methyl isothiocyanate, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, quintiofos, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfur, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, thetacypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin and zolaprofos.

Additionally, any combination of the above pesticides can be used.

The invention disclosed in this document can also be used with herbicides and fungicides, or both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14th Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of pesticide formulation types and international coding system" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one nonionic lipophilic surface-active agent, (2) at least one nonionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, nonionic, or mixtures of the two types. For wettable powder formulations, the most common dispersing agents are sodium lignosulfonates.

For suspension concentrates, very good adsorption and stabilization are obtained using polyelectrolytes, such as sodium naphthalene sulfonate formaldehyde condensates. Tristyrylphenol ethoxylate phosphate esters are also used. Nonionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzene sulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are nonionics: sorbitan monooleates; sorbitan monooleate ethoxylates; and methyl oleate esters.

Surfactants are sometimes used, either alone or with other additives such as mineral or vegetable oils as surfactants to spray-tank mixes to improve the biological performance of the pesticide on the target. The types of surfactants used for bioenhancement depend generally on the nature and mode of action of the pesticide. However, they are often nonionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ultra low volume formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduced more than fifty percent, preferably more than 90 percent, even more preferably 99 percent.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits. An example of such a use is spraying such plants with the invention disclosed in this document.

The invention disclosed in this document is suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

What is claimed is:

1. A composition comprising

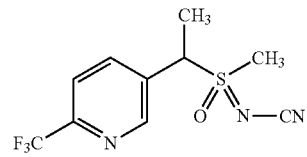

(a)

Compound A wherein said Compound A is at a concentration of about 0.1 to about 500 ppm;
(b) ammonium sulfate, wherein said ammonium sulfate is at a concentration of about 10,000 to about 22,000 ppm;
(c) nonionic surfactant, wherein said nonionic surfactant is at a concentration of about 500 to about 2500 ppm.

2. A process to control pests said process comprising applying a composition according to claim 1 to a locus inhabited or that can be inhabited by pests.

3. A process according to claim 2 wherein the amount of said composition is from about 0.01 grams per hectare to about 5000 grams per hectare.

4. A process according to claim 3 wherein said pests are one or more of the following Coleoptera, Dermaptera, Dictyoptera, Diptera, Hemiptera, Homoptera, Hymenoptera, Isoptera, Lepidoptera, Mallophaga, Orthoptera, Phthiraptera, Siphonaptera, Thysanoptera, Thysanura, Acarina, Nematoda, and Symphyla.

* * * * *